United States Patent
Wei

(10) Patent No.: US 11,452,544 B1
(45) Date of Patent: Sep. 27, 2022

(54) INTRA-CARDIAC MYOCARDIAL RESECTION DEVICE

(71) Applicant: Xiang Wei, Wuhan (CN)

(72) Inventor: Xiang Wei, Wuhan (CN)

( * ) Notice: Subject to any disclaimer, the term of this patent is extended or adjusted under 35 U.S.C. 154(b) by 49 days.

(21) Appl. No.: 17/243,958

(22) Filed: Apr. 29, 2021

(51) Int. Cl.
*A61B 17/3207* (2006.01)
*A61B 17/00* (2006.01)

(52) U.S. Cl.
CPC .......... *A61B 17/320783* (2013.01); *A61B 17/320708* (2013.01); *A61B 2017/00243* (2013.01); *A61B 2017/00438* (2013.01); *A61B 2017/00924* (2013.01)

(58) Field of Classification Search
CPC ........ A61B 2010/0208; A61B 10/0233; A61B 2017/00924; A61B 2017/00438; A61B 2017/00243; A61B 17/320708; A61B 17/320783
See application file for complete search history.

(56) References Cited

U.S. PATENT DOCUMENTS

| | | | |
|---|---|---|---|
| 8,906,052 | B1 | 12/2014 | Patel et al. |
| 2012/0078279 | A1* | 3/2012 | Mark ............... A61B 10/0275 606/171 |
| 2015/0327881 | A1* | 11/2015 | Willhite ........... A61B 17/32002 606/180 |
| 2018/0110540 | A1* | 4/2018 | Palushi .......... A61B 17/320758 |

FOREIGN PATENT DOCUMENTS

| | | |
|---|---|---|
| CN | 101365389 | 2/2009 |
| CN | 205286479 | 6/2016 |
| CN | 207306709 | 5/2018 |
| CN | 207768476 | 8/2018 |
| KR | 101811272 | 12/2017 |
| WO | 9839038 | 9/1998 |

OTHER PUBLICATIONS

First Office Action of priority appl. No. CN2018104020286 dated Mar. 8, 2019 and English translation.

* cited by examiner

*Primary Examiner* — Jocelin C Tanner

(57) ABSTRACT

An intra-cardiac myocardial resection device comprises an outer-layer protective sleeve and an inner-layer scalpel sleeve. An upper sidewall of the outer-layer protective sleeve is provided with a resection window, and an upper edge of the resection window is provided with a downward hook; and a sidewall of the outer-layer protective sleeve is provided with an axial sliding groove. The inner-layer scalpel sleeve is mounted in the outer-layer protective sleeve, and an upper end of the inner-layer scalpel sleeve is provided with an annular blade having an upward edge. A sidewall of the inner-layer scalpel sleeve is provided with a hollow operation handle, and the hollow operation handle extends out of the sliding groove. During a surgery, performed by using the intra-cardiac myocardial resection device, a resection extent and a resection effect can be monitored, and the surgical treatment effect for such patients is improved.

8 Claims, 9 Drawing Sheets

INTRA-CARDIAC MYOCARDIAL RESECTION DEVICE

CROSS-REFERENCE TO RELATED APPLICATIONS

This application is a U.S. Continuation of International Patent Application No. PCT/CN2018/118017 filed Nov. 28, 2018, which claims priority to Chinese patent application No. 201810402028.6, filed Apr. 28, 2018, the entire contents of which are incorporated herein by reference.

TECHNICAL FIELD

The present disclosure belongs to the technical field of minimally invasive cardiac surgical instruments, and particularly relates to an intra-cardiac myocardial resection device.

BACKGROUND

Hypertrophic obstructive cardiomyopathy is a disease of abnormal myocardial morphology, with an incidence of about 0.02%-0.2% in the population, namely one in about 500 people suffers from this disease. The pathogenesis may be related to gene mutation, abnormal myocardial calcium dynamics and increased secretion of catecholamines. The pathological manifestations of this disease include asymmetric ventricular septal hypertrophy, a reduced left ventricular volume due to hypertrophic myocardium protruding to a left ventricle, significant increase in pressure gradient of a left ventricular outflow tract, systolic anterior motion (SAM symptom) of a mitral valve and further aggravated obstruction of the left ventricular outflow tract, which results in obstruction of left ventricular ejection and progressive deterioration of cardiac function. The clinical symptoms of this disease are mainly manifested as chest pain, dyspnea, syncope and other heart failure symptoms. The annual mortality rate without treatment is 1.7%-4%, dominated by sudden death caused by malignant arrhythmia, with poor natural prognosis.

At present, treatment methods for hypertrophic obstructive cardiomyopathy mainly include drug therapy, dual-chamber pacing therapy, transcoronary ventricular septal alcohol ablation and open ventricular septal myocardial resection (Morrow surgical method and improved Morrow surgical method), among which the drug therapy and the dual-chamber pacing therapy can only reduce the myocardial oxygen consumption, alleviate the heart failure symptoms, and enhance the exercise tolerance of patients to a certain extent, but cannot remove the cause fundamentally, so that the treatment effect is limited. During the alcohol ablation, partial myocardial infarction is caused by injecting absolute alcohol into a first septal branch of a left anterior descending coronary artery, which makes a basal segment of a hypertrophic ventricular septal thinner, and realizes etiological treatment of reducing hypertrophic obstruction and pressure gradient. However, great limitations still exist in this method: (1) myocardial infarction in non-target areas may be caused, which results in abnormal myocardial motion, and worsen the condition; (2) high incidence (about 10%) of complications such as atrioventricular block and ventricular arrhythmia may be caused by myocardial scar formation; (3) the alcohol ablation is not applicable to about 5%-8% of patients due to variations in the first septal branch; (4) short-term and long-term treatment effects are both inferior to those of the open ventricular septal myocardial resection; and (5) papillary muscle deformities of the mitral valve and associated valvular structural abnormalities cannot be dealt with. In addition, a few heart centers have attempted ventricular septal radio-frequency ablation through percutaneous catheters, but large-scale application has not been realized due to many complications. Therefore, currently ventricular septal myocardial resection is still the best treatment method for hypertrophic obstructive cardiomyopathy.

Nevertheless, the traditional ventricular septal myocardial resection still faces many challenges and problems: (1) as the resection is performed in a heart arrested state, the thickness and texture of the heart at the moment are different from those of the heart in a beating state, a resection extent is difficult to evaluate before surgery and completely depends on the experience of a surgeon, and therefore such surgery can be successfully completed in only a few heart centers with rich experience, and is difficult to popularize; (2) as a resection effect cannot be evaluated in real time after resection, if the resection extent is overly wide, ventricular septal rupture and conductive fasciculus injury may be caused, and if the resection is not complete, the treatment effect of the surgery is poor; and (3) surgical trauma, myocardial injury and systemic inflammatory response may be caused by median thoracotomy, open heart surgery and extracorporeal circulation. Therefore, the surgical methods of ventricular septal myocardial resection still need to be improved urgently.

SUMMARY

In order to solve the problems above in the prior art, it is an object of the present disclosure to provide an intra-cardiac myocardial resection device.

The technical solution adopted by the present disclosure is as follows:

An intra-cardiac myocardial resection device comprises an outer-layer protective sleeve and an inner-layer scalpel sleeve, wherein an upper end of the outer-layer protective sleeve is bullet-shaped, a top end of the outer-layer protective sleeve is provided with an exhaust hole, an upper sidewall of the outer-layer protective sleeve is provided with a resection window, an upper edge of the resection window is provided with a downward hook, an outer sidewall of the outer-layer protective sleeve is provided with a handle, and a sidewall of the outer-layer protective sleeve is provided with an axial sliding groove; the inner-layer scalpel sleeve is mounted in the outer-layer protective sleeve, the inner-layer scalpel sleeve is in sliding fit with the outer-layer protective sleeve, an annular sealing ring is mounted between the inner-layer scalpel sleeve and the outer-layer protective sleeve, an upper end of the inner-layer scalpel sleeve is provided with an annular blade having an upward edge, a lower end of the inner-layer scalpel sleeve is closed, a sidewall of the inner-layer scalpel sleeve is provided with a hollow operation handle, and the hollow operation handle is communicated with an inner cavity of the inner-layer scalpel sleeve and extends out of the sliding groove.

Preferably, a circle of silica gel gasket adapted to the annular blade is mounted on the outer-layer protective sleeve, the silica gel gasket is positioned on the upper edge of the resection window, and the hook is positioned on an inner side of the silica gel gasket; and after the inner-layer scalpel sleeve moves upwards to close the annular blade and the silica gel gasket, the hook is positioned on an inner side of the annular blade.

Preferably, the hook is inclined outwards according to practical requirements at an inclination angle of 0-90 degrees.

Further, an upper end and a lower end of the sliding groove are respectively provided with a transverse bayonet.

Further, a lower end of the outer-layer protective sleeve is connected with the lower end of the inner-layer scalpel sleeve through a compression spring.

Preferably, the lower end of the outer-layer protective sleeve is connected with an end cover through threads, and the compression spring is positioned between the end cover and the inner-layer scalpel sleeve.

Preferably, an outer side of the end cover is provided with a lantern ring.

Further, two handles are provided, the two handles are respectively positioned on a left side and a right side of the sliding groove, and the handles are provided with lantern rings.

Further, a hollow channel of the hollow operation handle is provided with a syringe interface.

In order to further improve the stability of resection, the present disclosure also discloses a preferred technical solution:

an intra-cardiac myocardial resection device comprises an outer-layer protective sleeve, an inner-layer scalpel sleeve, and a core-layer push rod, wherein an upper end of the outer-layer protective sleeve is bullet-shaped, a top end of the outer-layer protective sleeve is provided with an exhaust hole, an upper sidewall of the outer-layer protective sleeve is provided with a resection window, an upper edge of the resection window is provided with a downward hook, and a sidewall of the outer-layer protective sleeve is provided with an axial sliding groove;

the inner-layer scalpel sleeve is sleeved in the outer-layer protective sleeve, the inner-layer scalpel sleeve is in sliding fit with the outer-layer protective sleeve, an annular sealing ring is mounted between the inner-layer scalpel sleeve and the outer-layer protective sleeve, an upper end of the inner-layer scalpel sleeve is provided with an annular blade having an upward edge, a lower end of the inner-layer scalpel sleeve extends out of a lower end of the outer-layer protective sleeve, and the lower end of the inner-layer scalpel sleeve is provided with an operation handle; and the core-layer push rod is sleeved in the inner-layer scalpel sleeve, the core-layer push rod is in sliding fit with the inner-layer scalpel sleeve, an annular sealing ring is mounted between the core-layer push rod and the inner-layer scalpel sleeve, an upper end of the core-layer push rod is provided with a puncture needle matched with the hook for use, a lower end of the core-layer push rod extends out of the lower end of the inner-layer scalpel sleeve, a lower portion of the core-layer push rod is provided with a stopper matched with the sliding groove for use, and the stopper is provided with a water injection channel penetrating to a front end of the core-layer push rod.

Further, the lower end of the core-layer push rod is provided with a guide wire channel communicated with the front end of the core-layer push rod.

Preferably, an outer surface of the outer-layer protective sleeve is coated with a coating for preventing metal from generating an acoustic shadow under echocardiography.

The present disclosure has the following beneficial effects:

the present disclosure is simple in structure, convenient to operate and reliable in use, can significantly shorten the surgical time, and creates a brand-new minimally invasive surgical method for treating hypertrophic obstructive cardiomyopathy; through transesophageal echocardiography guidance, the resection effect of surgery can be evaluated in real time, so that on the one hand, the potential problem of excessive myocardial resection due to static heart resection is avoided, and the risk of iatrogenic ventricular septal rupture is eluded, and on the other hand, the problem of poor treatment effect caused by an insufficient resection extent of surgery is also avoided, so that excessive dependence on the experience of a surgeon is reduced, and the treatment effect of surgery is significantly improved; the structure designed by the present disclosure integrates the functions of tissue resection and recovery, and thus peripheral artery embolism caused by falling of resected tissue is prevented; the hook at a head end of the present disclosure can stably anchor myocardium in target areas, so that off-target resection of the myocardium is prevented; the present disclosure is made of a material with good ultrasonic compatibility, and thus is convenient for performing esophageal ultrasonic guidance; surgical trauma caused by median thoracotomy is avoided through a tiny incision in the left anterior chest wall, and postoperative recovery of a patient is fast; the application of extracorporeal circulation in conventional open heart surgery is avoided in surgery performed in a heart beating state, so that myocardial ischemia reperfusion injury and complications related to extracorporeal circulation are avoided; and if unpredictable complications occur in the surgery, the conventional thoracotomy can be timely performed, thereby greatly avoiding fatal complications caused by alcohol ablation and radio-frequency ablation.

DETAILED DESCRIPTION OF THE EMBODIMENTS

The present disclosure will be further elucidated with reference to the drawings and specific examples.

Example 1

Figure 1:
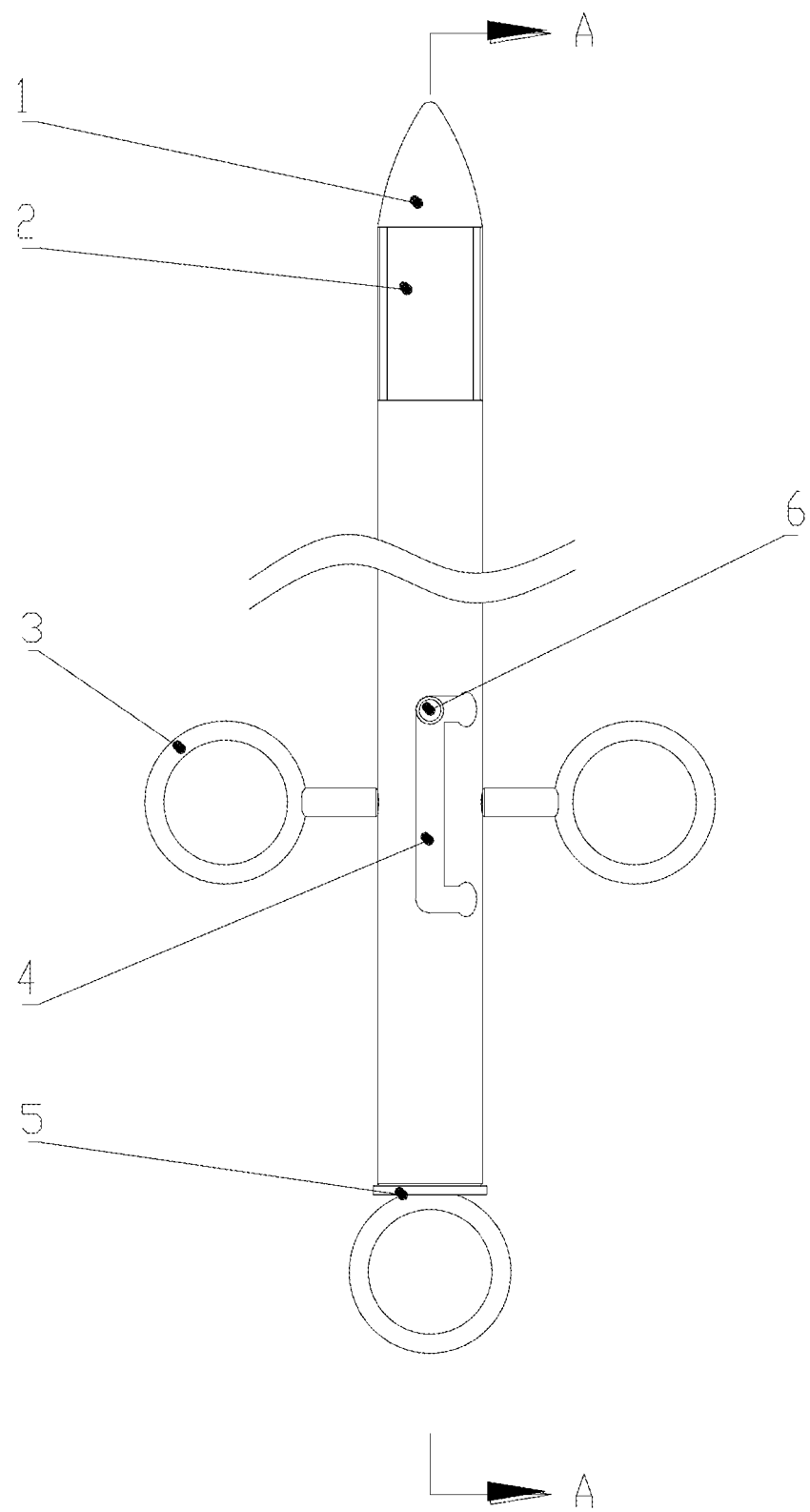
FIG. 1 is a schematic structural view of Example 1 of the present disclosure.
Figure 2:
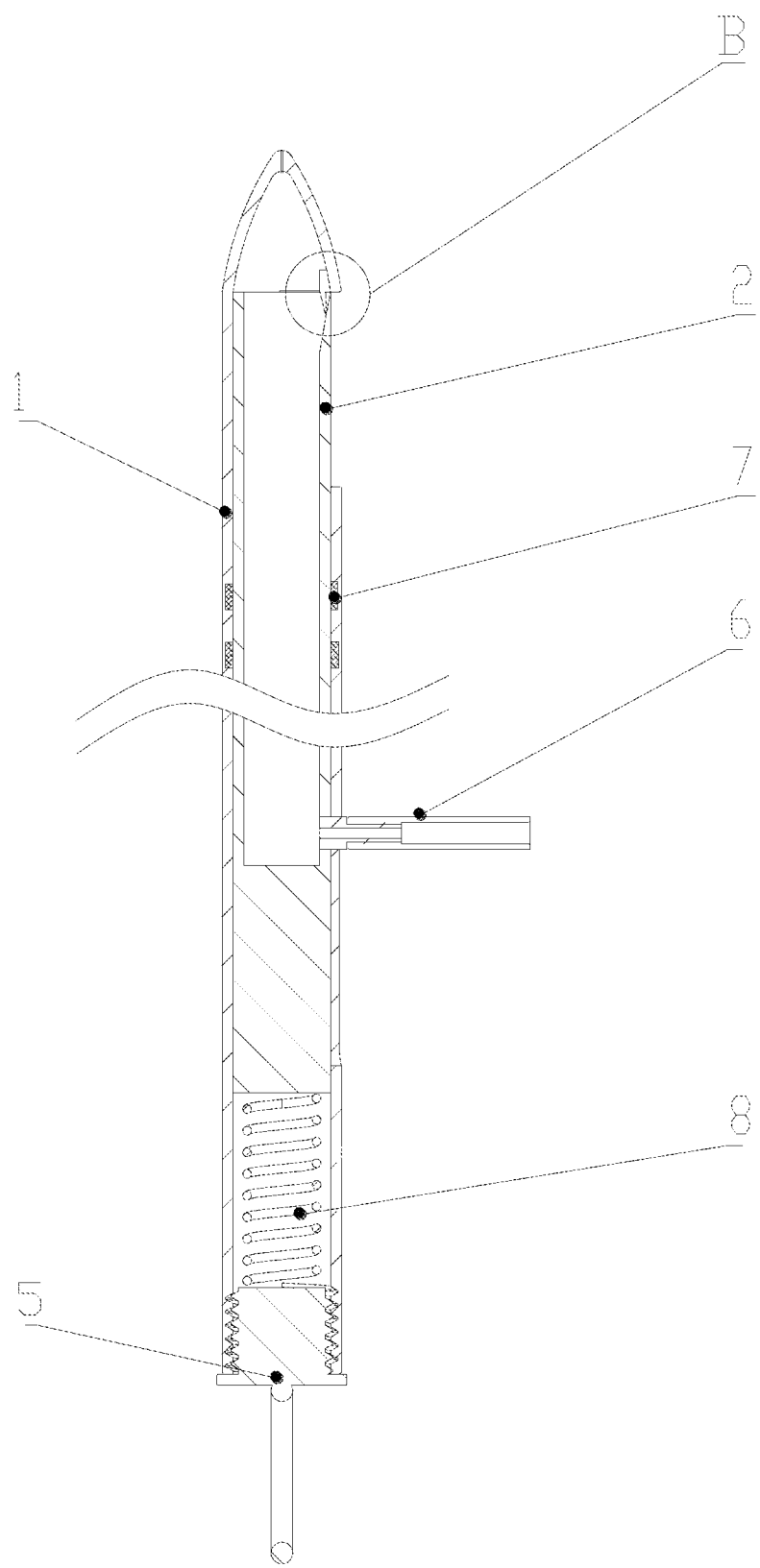
FIG. 2 is a sectional view A-A of FIG. 1.
Figure 3:
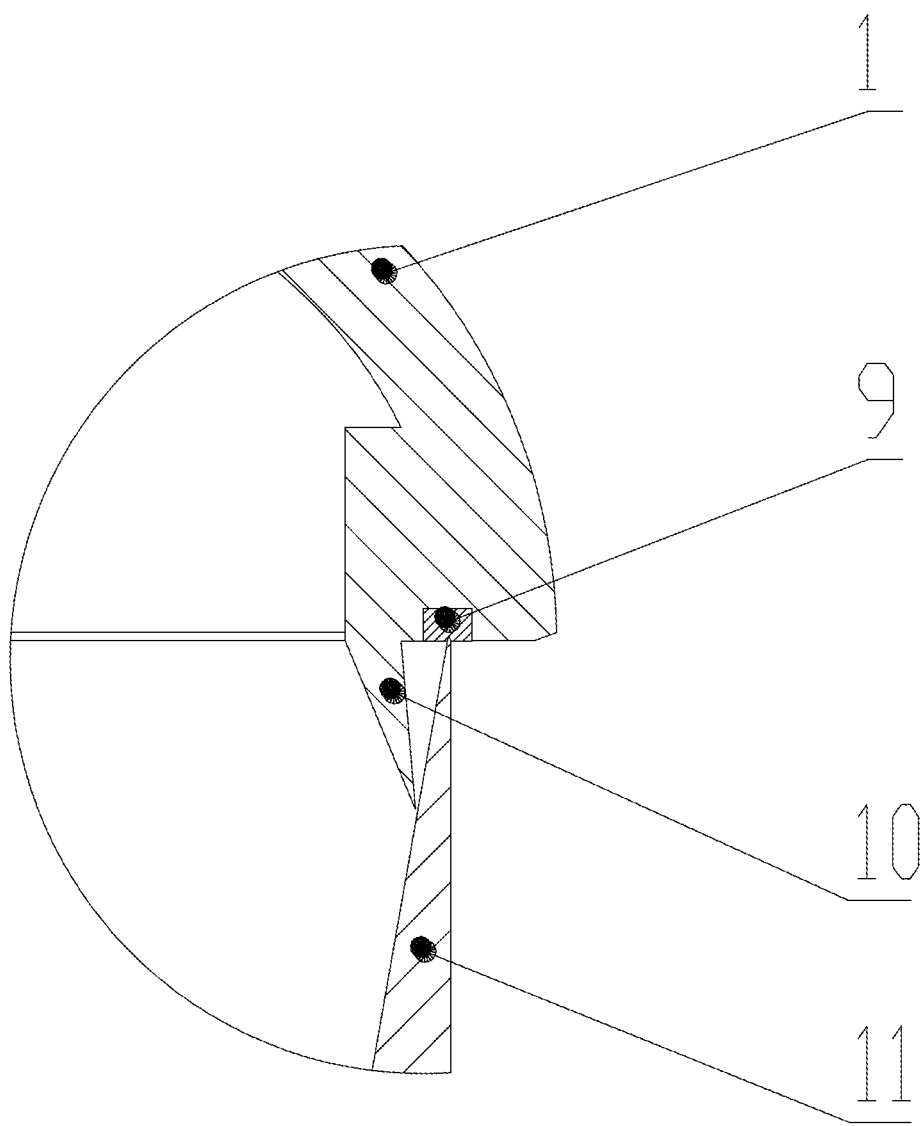
FIG. 3 is an enlarged schematic view of a part B of FIG. 2.
Figure 4:
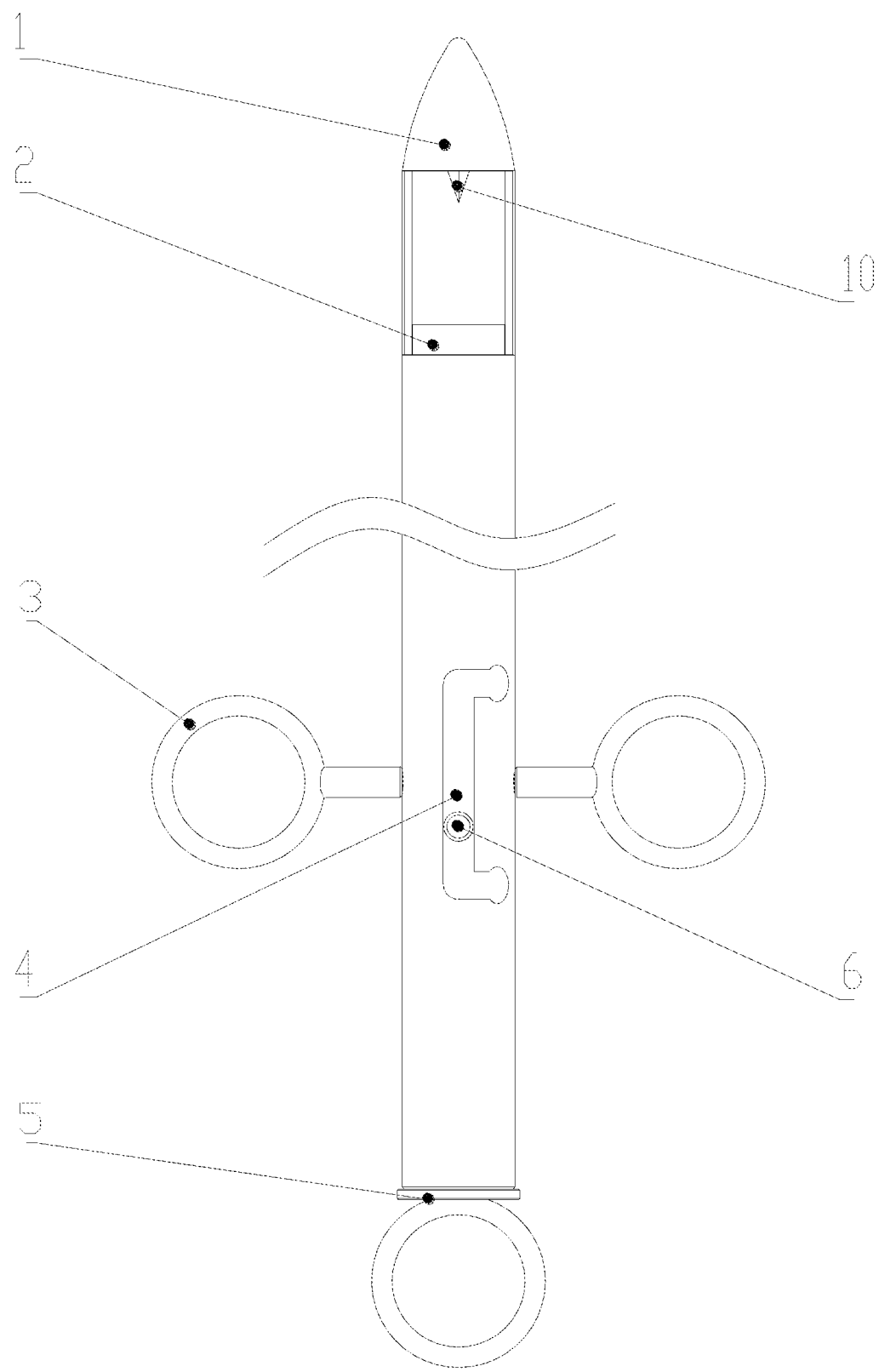
FIG. 4 is a schematic view showing Example 1 of the present disclosure in a using state.

As shown in FIGS. 1-4, an intra-cardiac myocardial resection device of the example comprises an outer-layer protective sleeve 1 and an inner-layer scalpel sleeve 2, an upper end of the outer-layer protective sleeve 1 is bullet-shaped, a top end of the outer-layer protective sleeve 1 is provided with an exhaust hole, the bullet-shaped end is beneficial to being inserted into cardiac tissue, and meanwhile injury of the tissue is reduced to the greatest extent; an upper sidewall of the outer-layer protective sleeve 1 is provided with a resection window, so that a protruded hypertrophic obstruction part can be placed therein, and meanwhile a sleeve wall on a rear side of the resection window can protect cardiac tissue behind the resection device and prevent the cardiac tissue from being injured accidentally by the inner-layer scalpel sleeve 2; an upper edge of the resection window is provided with a downward hook 10 for anchoring pre-resected hypertrophic myocardium in target areas, preventing the resection device from slipping off, fixing a resection thickness and providing a reverse shearing force for the inner-layer scalpel sleeve 2; an outer sidewall of the outer-layer protective sleeve 1 is provided with a handle 3, so that operation is convenient; a sidewall of the outer-layer protective sleeve 1 is provided with an axial sliding groove 4, and a length of the sliding groove 4 defines a moving distance of the inner-layer scalpel sleeve 2; the inner-layer scalpel sleeve 2 is mounted in the outer-layer protective sleeve 1, and the inner-layer scalpel sleeve 2 is in sliding fit with the outer-layer protective sleeve 1, so that the inner-layer scalpel sleeve 2 can slide back and forth along an axial direction of the outer-layer protective sleeve 1; an annular sealing ring 7 is mounted between the inner-layer scalpel sleeve 2 and the outer-layer protective sleeve 1, so that intra-cardiac high-pressure blood can be prevented from leaking out along a gap between the inner sleeve and the outer sleeve after entry of the resection device; an upper end of the inner-layer scalpel sleeve 2 is provided with an annular blade 11 having an upward edge for performing resection when moving upwards; a lower end of the inner-layer scalpel sleeve 2 is closed, and then forms a cavity together with the outer-layer protective sleeve 1; a sidewall of the inner-layer scalpel sleeve 2 is provided with a hollow operation handle 6, and the hollow operation handle 6 is communicated with an inner cavity of the inner-layer scalpel sleeve 2 and can be used for liquid sealing of heparin brine and removing air in the cavity; and the hollow operation handle 6 extends out of the sliding groove 4, so that the operation is convenient.

A method for using this example is as follows: in a process of performing hypertrophic myocardium resection, the resection device enters a pericardium through a tiny incision in a gap between the fourth rib and the fifth rib on the left anterior chest wall of a patient, the cardiac apex is exposed, a pouch is made at the cardiac apex, a tiny incision is made with a scalpel at the center of the pouch to the left ventricular cavity, and then the pouch is tightened. The inner-layer scalpel sleeve 2 is pushed to the upper end, the resection window is closed, the hollow operation handle 6 is connected with a syringe to perform pre-filling liquid sealing of heparin brine and remove air in the outer-layer protective sleeve 1. The upper end of the resection device of the present disclosure is fed into the left ventricular cavity along the incision in the cardiac apex, and positioned to a basal segment of hypertrophic ventricular septal to be resected under the guidance of transesophageal echocardiography and esophageal three-dimensional echocardiography, the resection window of the outer-layer protective sleeve 1 is aligned with a target area for resection, the hollow operation handle 6 is pulled downwards to open the resection window, and the hook 10 punctures into myocardial tissue in the target area and is anchored, no injury of chordae tendineae and papillary muscles is confirmed again under three-dimensional echocardiography, and the hollow operation handle 6 is pushed upwards to enable the hollow operation handle 6 to move upwards, the myocardial tissue in the target area is resected by the annular blade 11, and the resection device of the present disclosure is slowly withdrawn after resection of the tissue is confirmed. The withdrawn resection device of the present disclosure is opened and the resected myocardial tissue is removed, and the outer-layer protective sleeve 1 and the inner-layer scalpel sleeve 2 are washed with the heparin brine. The resection effect is examined under transesophageal echocardiography, and pressure gradient in the left ventricular outflow tract is measured by Doppler ultrasonography. If the resection extent is unsatisfactory, the resection device enters the pericardium again to repeat the resection process above so as to expand the resection extent until the surgical effect is satisfactory. The hollow operation handle 6 can be connected to a manometric catheter if necessary, and the pressure gradient in the left ventricular outflow tract is measured by the resection device of the present disclosure. The incision in the cardiac apex is sutured after the surgery is completed, and the incisions in the chest wall are closed layer by layer.

In order to resect tissue conveniently, a circle of silica gel gasket 9 adapted to the annular blade 11 is mounted on the outer-layer protective sleeve 1, the silica gel gasket 9 is positioned on the upper edge of the resection window, and the hook 10 is positioned on an inner side of the silica gel gasket 9; after the inner-layer scalpel sleeve 2 moves upwards to close the annular blade 11 and the silica gel gasket 9, and the hook 10 is positioned on an inner side of the annular blade 11, so that tissue that the resection device passes by can be prevented from being injured accidentally when the resection device of the present disclosure is fed into the heart. The silica gel gasket 9 is convenient to provide a reverse shearing force for the annular blade 11 as a board during resection of tissue, so that muscular tissue is easier to resect, and meanwhile liquid sealing can be provided for the inner-layer scalpel sleeve 2.

In order to enable the hook 10 to more easily fix the hooked tissue to be resected, the hook 10 is inclined outwards, and according to the thickness of myocardium to be resected, the inclination can be designed to be at different angles. The larger the angle between the hook and an axis of the resection device of the present disclosure is, the greater the resection thickness will be. An inclination angle can be selected as 0-90 degrees.

In order to improve the safety, an upper end and a lower end of the sliding groove 4 are respectively provided with a transverse bayonet. The bayonet at the upper end is a safety device for ensuring a normally closed state of the resection window, preventing other tissue from being injured accidentally caused by opening of the resection window, and preventing the resected tissue from falling off after resection is completed caused by opening of the resection window; and the bayonet at the lower end is a fixing device, after entering a target position in the cardiac chamber, the hollow operation handle 6 is pulled downwards and clamped into the bayonet at the lower end, the resection window is maintained in an opening state, so as to be convenient to operate the hook 10 and fix the target myocardial tissue.

In order to further improve the safety, the lower end of the outer-layer protective sleeve 1 is connected with the lower end of the inner-layer scalpel sleeve 2 through the compression spring 8 for maintaining the normally closed state of the resection window.

In order to facilitate installation and replacement of the compression spring 8, the lower end of the outer-layer protective sleeve 1 is connected with the end cover 5 through threads, and the compression spring 8 is positioned between the end cover 5 and the inner-layer scalpel sleeve 2.

In order to conveniently tighten the end cover 5, the outer side of the end cover 5 is provided with a lantern ring, and hand-held operation is convenient.

In order to facilitate operation, two handles 3 are provided, the two handles 3 are respectively positioned on a left side and a right side of the sliding groove 4, the handles 3 are provided with lantern rings, and fingers extend into the lantern rings, so that the operation is more convenient.

In order to ensure the liquid sealing, exhaust, pressure measurement and washing of the inner-layer scalpel sleeve 2, a hollow channel of the hollow operation handle 6 is provided with a syringe interface.

Example 2

Figure 5:
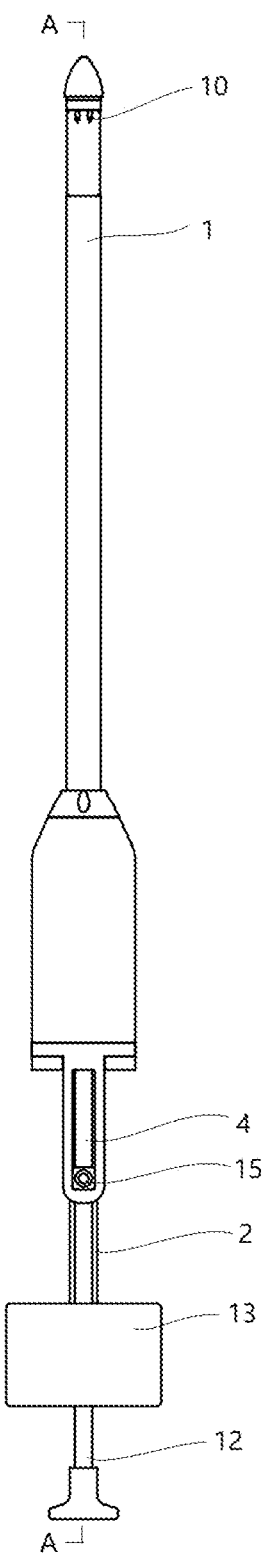
FIG. 5 is a schematic structural view of Example 2 of the present disclosure.
Figure 6:
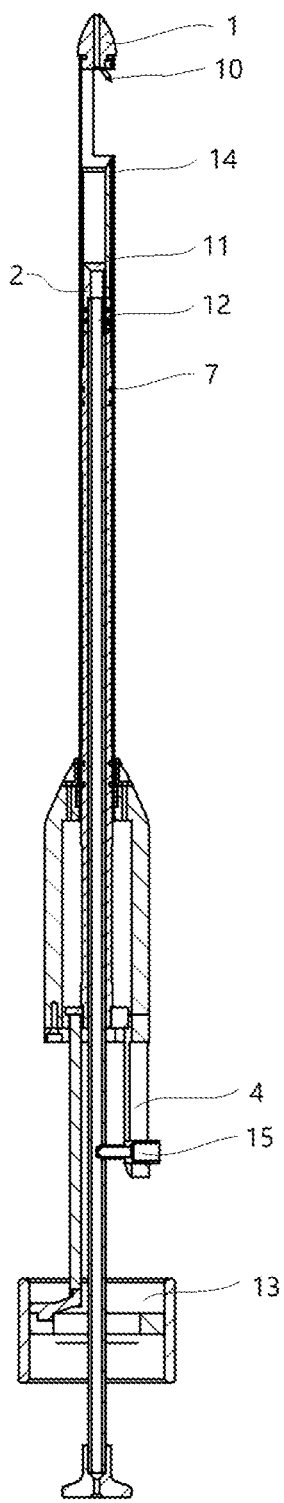
FIG. 6 is a sectional view A-A of FIG. 5.
Figure 7:
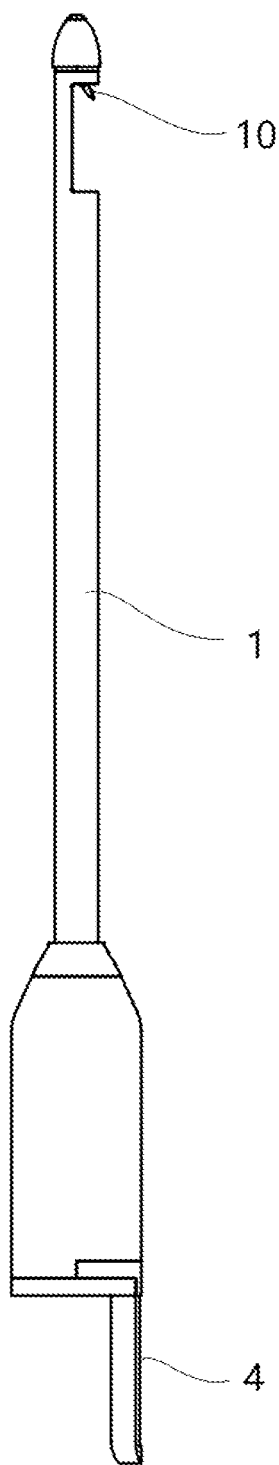
FIG. 7 is a schematic structural view of an outer-layer protective sleeve in Example 2 of the present disclosure.
Figure 8:
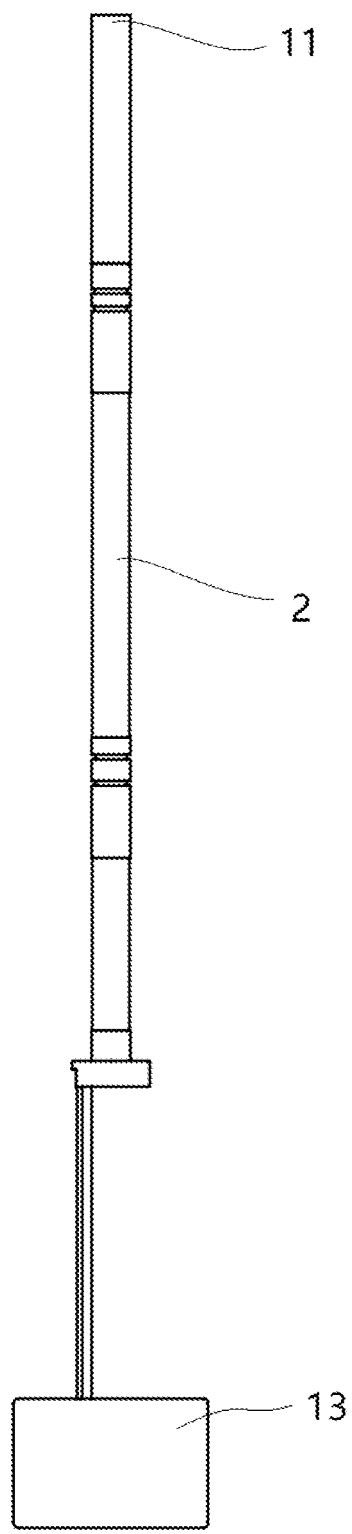
FIG. 8 is a schematic structural view of an inner-layer scalpel sleeve in Example 2 of the present disclosure.
Figure 9:
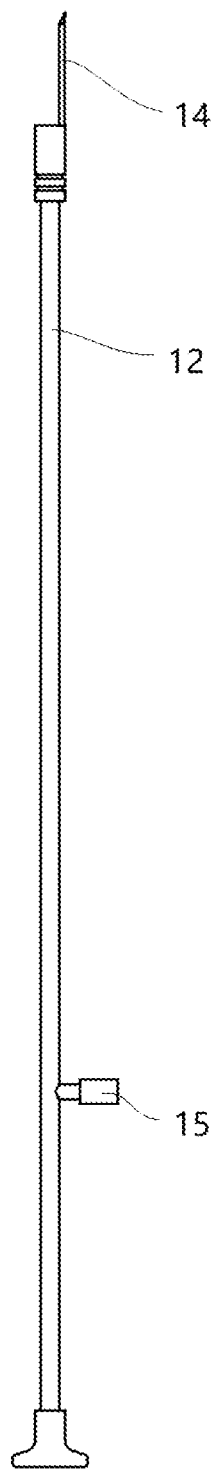
FIG. 9 is a schematic structural view of a core-layer push rod in Example 2 of the present disclosure.

As shown in FIGS. 5-9, an intra-cardiac myocardial resection device of the present disclosure comprises an outer-layer protective sleeve 1, an inner-layer scalpel sleeve 2 and a core-layer push rod 12, an upper end of the outer-layer protective sleeve 1 is bullet-shaped, the bullet-shaped end is beneficial to being inserted into cardiac tissue, and meanwhile injury of the tissue is reduced to the greatest extent; a top end of the outer-layer protective sleeve 1 is provided with an exhaust hole; an upper sidewall of the outer-layer protective sleeve 1 is provided with a resection window, so that a protruded hypertrophic obstruction part can be placed therein, and meanwhile a sleeve wall on a rear side of the resection window can protect cardiac tissue behind the resection device and prevent the cardiac tissue from being injured accidentally by the inner-layer scalpel sleeve 2; an upper edge of the resection window is provided with a downward hook 10 for anchoring pre-resected hypertrophic myocardium in target areas, preventing the resection device from slipping off, fixing a resection thickness and providing a reverse shearing force for the inner-layer scalpel sleeve 2; a sidewall of the outer-layer protective sleeve 1 is provided with an axial sliding groove 4; the inner-layer scalpel sleeve 2 is sleeved in the outer-layer protective sleeve 1, and the inner-layer scalpel sleeve 2 is in sliding fit with the outer-layer protective sleeve 1, so that the inner-layer scalpel sleeve 2 can slide back and forth along an axial direction of the outer-layer protective sleeve 1; an annular sealing ring 7 is mounted between the inner-layer scalpel sleeve 2 and the outer-layer protective sleeve 1, so that intra-cardiac high-pressure blood can be prevented from leaking out along a gap between the inner sleeve and the outer sleeve after entry of the resection device; an upper end of the inner-layer scalpel sleeve 2 is provided with an annular blade 11 having an upward edge for performing resection when moving upwards; a lower end of the inner-layer scalpel sleeve 2 extends out of the lower end of the outer-layer protective sleeve 1, and the lower end of the inner-layer scalpel sleeve 2 is provided with an operation handle 13, so that on the one hand, the inner-layer scalpel sleeve 2 can be pushed to move upwards, and on the other hand, the inner-layer scalpel sleeve 2 can be rotated to perform resection; the core-layer push rod 12 is sleeved in the inner-layer scalpel sleeve 2, the core-layer push rod 12 is in sliding fit with the inner-layer scalpel sleeve 2, and an annular sealing ring 7 is mounted between the core-layer push rod 12 and the inner-layer scalpel sleeve 2, so that intra-cardiac high-pressure blood can be prevented from leaking out along a gap between the core-layer push rod 12 and the inner-layer scalpel sleeve 2 after entry of the resection device; a puncture needle 14 matched with the hook 10 for use is mounted at an upper end of the core-layer push rod 12, the hook 10 and the puncture needle 14 can penetrate into myocardial tissue in target areas from an upper direction and a lower direction so as to ensure the anchoring stability, a lower end of the core-layer push rod 12 extends out of the lower end of the inner-layer scalpel sleeve 2, a lower portion of the core-layer push rod 12 is provided with a stopper 15 matched with the sliding groove 4 for use, and the stopper 15 can only move along an axial direction in the sliding groove 4, so that a position relation between the puncture needle 14 and the hook 10 is ensured, and the stopper 15 is provided with a water injection channel penetrating to a front end of the core-layer push rod 12 for liquid sealing of heparin brine and removing air in the cavity.

A method for using this example is as follows: in a process of performing hypertrophic myocardium resection, the resection device enters a pericardium through a tiny incision in a gap between the fourth rib and the fifth rib on the left anterior chest wall of a patient, the cardiac apex is exposed, a pouch is made at the cardiac apex, a sheath tube is used for puncturing to the left ventricle at the center of the pouch, a guide wire is fed into the left ventricle, the sheath tube is withdrawn from the left ventricle, an entrance to the cardiac apex is enlarged with a dilator along the guide wire, and the pouch is tightened while withdrawing the dilator. The inner-layer scalpel sleeve 2 is pushed to the upper end with the operation handle 13, the resection window is closed, the water injection channel of the stopper 15 is connected with a syringe to perform pre-filling liquid sealing of heparin brine and remove air in the outer-layer protective sleeve 1. The upper end of the resection device of the present disclosure is fed into the left ventricular cavity along the guide wire, and positioned to a basal segment of hypertrophic ventricular septal to be resected under the guidance of transesophageal echocardiography and esophageal three-dimensional echocardiography, the resection window of the outer-layer protective sleeve 1 is aligned with a target area for resection, the operation handle 13 is pulled downwards to open the resection window, and the hook 10 punctures into myocardial tissue in the target area and is anchored, no injury of chordae tendineae and papillary muscles is confirmed again under three-dimensional echocardiography, and the core-layer push rod 12 is pushed upwards to enable the puncture needle 14 to puncture into myocardial tissue in the target areas from bottom to top and to be anchored; and then the operation handle 13 is pushed upwards to enable the operation handle 13 to move upwards, and the operation handle 13 can be rotated around a central axis simultaneously, so that the myocardial tissue in the target areas is resected by the annular blade 11, and the resection device of the present disclosure is slowly withdrawn after resection of the tissue is confirmed. The withdrawn resection device of the present disclosure is opened and the resected myocardial tissue is removed, and the outer-layer protective sleeve 1 and the inner-layer scalpel sleeve 2 are washed with the heparin brine. The resection effect is examined under transesophageal echocardiography, and pressure gradient in the left ventricular outflow tract is measured by Doppler ultrasonography. If the resection extent is unsatisfactory, the resection device enters the pericardium again to repeat the resection process above so as to expand the resection extent until the surgical effect is satisfactory. The water injection channel of the stopper 15 can be connected to a manometric catheter if necessary, and the pressure gradient in the left ventricular outflow tract is measured by the resection device of the present disclosure. The incision in the cardiac apex is sutured after the surgery is completed, and the incisions in the chest wall are closed layer by layer.

In order to facilitate the rotation operation, the operation handle 13 can be designed to be in an annular shape, the operation handle 13 is coaxial with the inner-layer scalpel sleeve 2, and the operation handle 13 is fixedly connected with the inner-layer scalpel sleeve 2 through a connecting arm.

In order to improve the positioning accuracy of the resection device and the guiding function of the guide wire, the lower end of the core-layer push rod 12 is provided with a guide wire channel communicated with the front end of the core-layer push rod 12, and the guide wire can penetrate through an opening at the top end and penetrate out of the lower end of the core-layer push rod 12.

In order to avoid the influence of the resection device made of a metal material on an ultrasonic image, an outer surface of the outer-layer protective sleeve 1 is coated with a coating for preventing metal from generating an acoustic shadow under echocardiography.

In order to resect tissue conveniently, a circle of silica gel gasket 9 adapted to the annular blade 11 is mounted on the outer-layer protective sleeve 1, the silica gel gasket 9 is positioned on the upper edge of the resection window, and the hook 10 is positioned on the inner side of the silica gel gasket 9; after the inner-layer scalpel sleeve 2 moves upwards to close the annular blade 11 and the silica gel gasket 9, the hook 10 is positioned on the inner side of the annular blade 11, so that tissue that the resection device passes by can be prevented from being injured accidentally when the resection device of the present disclosure is fed into the heart. The silica gel gasket 9 is convenient to provide a reverse shearing force for the annular blade 11 as a board during resection of tissue, so that muscular tissue is easier to resect, and meanwhile liquid sealing can be provided for the inner-layer scalpel sleeve 2.

In order to enable the hook 10 to more easily fix the hooked tissue to be resected, the hook 10 is inclined outwards, and according to the thickness of myocardium to be resected, the inclination can be designed to be at different angles. The larger the angle between the hook and an axis of the resection device of the present disclosure is, the greater the resection thickness will be. An inclination angle can be selected as 0-90 degrees.

In order to ensure the liquid sealing, exhaust, pressure measurement and washing of the inner-layer scalpel sleeve 2, the water injection channel of the stopper 15 is provided with a syringe interface.

The present disclosure is not limited to the above-described alternative embodiments, and any person skilled in the art can obtain other products in various forms under the inspiration of the present disclosure. Despite any change in the shape or structure thereof, technical solutions falling within the scope defined by the claims of the present disclosure all fall within the protection scope of the present disclosure.

What is claimed is:

1. An intra-cardiac myocardial resection device, comprising an outer-layer protective sleeve (1) and an inner-layer scalpel sleeve (2), wherein an upper end of the outer-layer protective sleeve (1) is bullet-shaped, a top end of the outer-layer protective sleeve (1) is provided with an exhaust hole, an upper sidewall of the outer-layer protective sleeve (1) is provided with a resection window, an upper edge of the resection window is provided with a downward hook (10), an outer sidewall of the outer-layer protective sleeve (1) is provided with handles (3), and a sidewall of the outer-layer protective sleeve (1) is provided with an axial sliding groove (4); the inner-layer scalpel sleeve (2) is mounted in the outer-layer protective sleeve (1), the inner-layer scalpel sleeve (2) is in sliding fit with the outer-layer protective sleeve (1), an annular sealing ring (7) is mounted between the inner-layer scalpel sleeve (2) and the outer-layer protective sleeve (1), an upper end of the inner-layer scalpel sleeve (2) is provided with an annular blade (11) having an upward edge, a lower end of the inner-layer scalpel sleeve (2) is closed, a sidewall of the inner-layer scalpel sleeve (2) is provided with a hollow operation handle (6), and the hollow operation handle (6) is communicated with an inner cavity of the inner-layer scalpel sleeve (2) and extends out of the sliding groove (4); a circle of silica gel gasket (9) adapted to the annular blade (11) is mounted on the outer-layer protective sleeve (1), the silica gel gasket (9) is positioned on the upper edge of the resection window, and the hook (10) is positioned on an inner side of the silica gel gasket (9); and after the inner-layer scalpel sleeve (2) moves upwards to close the annular blade (11) and the silica gel gasket (9), the hook (10) is positioned on an inner side of the annular blade (11).

2. The intra-cardiac myocardial resection device according to claim 1, wherein the hook (10) is inclined outwards at an inclination angle of 0-90 degrees.

3. The intra-cardiac myocardial resection device according to claim 1, wherein an upper end and a lower end of the sliding groove (4) are respectively provided with a transverse bayonet.

4. The intra-cardiac myocardial resection device according to claim 3, wherein a lower end of the outer-layer protective sleeve (1) is connected with a lower end of the inner-layer scalpel sleeve (2) through a compression spring (8).

5. The intra-cardiac myocardial resection device according to claim 4, wherein the lower end of the outer-layer protective sleeve (1) is connected with an end cover (5) through threads, and the compression spring (8) is positioned between the end cover (5) and the inner-layer scalpel sleeve (2).

6. The intra-cardiac myocardial resection device according to claim 5, wherein an outer side of the end cover (5) is provided with a lantern ring.

7. The intra-cardiac myocardial resection device according to claim 1, wherein two handles (3) are provided, the two handles (3) are respectively positioned on a left side and a right side of the sliding groove (4), and the handles (3) are provided with lantern rings.

8. The intra-cardiac myocardial resection device according to claim 1, wherein a hollow channel of the hollow operation handle (6) is provided with a syringe interface.

* * * * *

UNITED STATES PATENT AND TRADEMARK OFFICE
CERTIFICATE OF CORRECTION

| | | |
|---|---|---|
| PATENT NO. | : 11,452,544 B1 | Page 1 of 1 |
| APPLICATION NO. | : 17/243958 | |
| DATED | : September 27, 2022 | |
| INVENTOR(S) | : Xiang Wei | |

It is certified that error appears in the above-identified patent and that said Letters Patent is hereby corrected as shown below:

On the Title Page

Add Item (60):
"This application is a U.S. Continuation of International Patent Application No. PCT/CN2018/118017 filed Nov. 28, 2018, which claims priority to Chinese patent application No. 2018104020286, filed Apr. 28, 2018, the entire contents of which are incorporated herein by reference."

Signed and Sealed this
Fourth Day of February, 2025

Coke Morgan Stewart
*Acting Director of the United States Patent and Trademark Office*